United States Patent [19]

Choudhury et al.

[11] Patent Number: 5,235,100
[45] Date of Patent: Aug. 10, 1993

[54] PREPARATION OF OPTICALLY ACTIVE ALIPHATIC CARBOXYLIC ACIDS

[75] Inventors: Azfar A. Choudhury; Abbas Kadkhodayan; Deepak R. Patil, all of Orangeburg, S.C.

[73] Assignee: Ethyl Corporation, Richmond, Va.

[21] Appl. No.: 825,630

[22] Filed: Jan. 24, 1992

[51] Int. Cl.$^5$ ............................................. C07B 57/00
[52] U.S. Cl. ...................... 562/401; 548/531; 549/71; 549/499; 558/414; 560/9; 560/56; 560/59; 560/61; 560/100; 560/102; 560/105; 560/125; 560/126; 560/128; 560/147
[58] Field of Search .................... 562/401; 548/531; 549/71, 499; 560/9, 56, 59, 61, 100, 102, 105, 147, 125, 126, 128; 558/414

[56] References Cited

U.S. PATENT DOCUMENTS

| | | | |
|---|---|---|---|
| 4,694,100 | 9/1987 | Shimizu et al. | 560/105 |
| 4,723,033 | 2/1988 | Erickson | 560/56 |
| 4,752,417 | 6/1988 | Inoue et al. | 562/401 |
| 4,831,147 | 5/1989 | Russell | 562/401 X |
| 4,973,745 | 11/1990 | Blaschke et al. | 562/401 |
| 4,983,765 | 1/1991 | Lukas et al. | 562/401 |
| 5,015,764 | 5/1991 | Manimaran et al. | 562/401 |

Primary Examiner—Jose G. Dees
Assistant Examiner—Vera C. Clarke
Attorney, Agent, or Firm—Richard J. Hammond

[57] ABSTRACT

A process for the separation of a racemic mixture of certain aliphatic carboxylic acids or esters thereof is disclosed. The process comprises:

i) separating a racemic mixture of an aliphatic carboxylic acid or ester thereof having the formula:

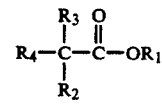

where $R_1$ is hydrogen or $C_1$ to $C_6$ linear or branched alkyl; $R_2$, $R_3$ and $R_4$ are different and are hydrogen or $C_1$ to $C_6$ linear or branched alkyl; cycloalkyl; alkyl-substituted cycloalkyl; $C_6$ to $C_{14}$ aryl; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; or $C_4$ to $C_5$ heteroaryl; which comprises:

ii) adding an inorganic or organic base to said first homogeneous melt thereby producing a second homogeneous melt;

iii) treating said second homogeneous melt with a chiral organic nitrogenous base;

iv) precipitating from the reaction melt mixture formed in step iii) a solid salt that is the reaction product of the chiral organic nitrogenous base and one of the diastereomers in said racemic mixture of the aliphatic carboxylic acid or ester thereof; and v) separating the precipitated salt.

23 Claims, No Drawings

PREPARATION OF OPTICALLY ACTIVE ALIPHATIC CARBOXYLIC ACIDS

FIELD OF INVENTION

This invention relates to the preparation of optically active carboxylic acids and the esters thereof. More particularly this invention relates to the preparation of aliphatic carboxylic acids and the esters thereof by first forming the diastereomeric salts of such materials and then separating the diastereomeric salts.

BACKGROUND OF THE INVENTION

Resolution of racemic aryl-substituted aliphatic carboxylic acids has been described in the literature. Kaiser et al, *J. Pharm. Sci.*, Vol. 65, No. 2, 269-273 (February 1976) formed the S(−)-α-methylbenzylamine salt of S(+)-ibuprofen, removed it from the reaction mixture by filtration and recrystallized it from isopropanol and then from methanol. After acidifying with 3N aqueous sulfuric acid and extracting with ether, S(+)-ibuprofen was obtained, m.p. 50-14 52·, $[\alpha]_D + 57$·with 95% optical purity as determined by GLC analysis. Cox et al., *J. Pharmacol. Exp. Ther.*, Vol. 232, No. 3, 636-643 (March 1985), using Kaiser et al.'s method, were able to obtain an S(+)-ibuprofen preparation which was 99% S-isomer and 1% R-isomer (w/w).

Other methods of separating the enantiomers of racemates can be effected by preparing a salt of the acid with an alkaloid or similar resolving agent such as cinchonidine, then separating the products by fractional crystallization from a solvent in which the salt of the dextrorotatory isomer is least soluble. The (+)-salt can then be acid cleaved to yield pure enantiomer. See, for example, U.S. Pat. No. 4,209,638, issued Jun. 24, 1980, U.S. Pat. No. 3,637,767, issued Jan. 25, 1972, which relates to resolution of naproxen and related compounds.

U.S. Pat. No. 5,015,764 discloses a process for separation of diastereomers of certain aliphatic carboxylic acid by first treating a solution of such carboxylic acids with a base and then adding a chiral organic nitrogenous base having a base strength no grater than the organic or inorganic base. One of the enantiomeric salts resulting from the reaction is less soluble in the reaction solution than the other. It precipitates and is separated.

In all of the aforementioned examples, an inert solvent is added to facilitate the reaction.

According to the present invention, there is provided a process for increasing the amount of the desired enantiomer obtained from a racemic mixture of $C_1$ to $C_6$ linear or branched aliphatic carboxylic acid or ester thereof in the absence of any additional solvent. The process comprises:

i) heating a solid racemic mixture of said aliphatic carboxylic acid or ester thereof to a temperature sufficient to produce a first homogenous salt;

ii) adding to said first homogenous melt an organic or inorganic base thereby producing a second homogenous melt;

iii) treating the second homogenous melt with a chiral organic nitrogenous base;

iv) precipitating from the reaction mixture formed in step iii) a solid salt that is the reaction product of the chiral organic nitrogenous base and one of the diastereomers of said racemic mixture of the aliphatic carboxylic acid or ester thereof; and v) separating the precipitated salt.

The $C_1$ to $C_6$ linear or branched aliphatic carboxylic acids and esters useful in the process of the present invention have the formula:

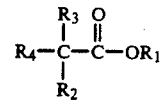

where $R_1$ is hydrogen or $C_1$ to $C_6$ linear or branched alkyl, $R_2$, $R_3$ and $R_4$ are different and are hydrogen or $C_1$ to $C_6$ linear or branched alkyl, e.g., methyl or ethyl; aralkyl, e.g., benzyl; cycloalkyl, e.g., cyclopropyl, cyclobutyl, cyclopentyl, cyclohexyl; alkyl substituted cycloalkyl, e.g., methylcyclohexyl; $C_6$ to $C_{10}$ aryl, e.g., phenyl unsubstituted or substituted with for example methyl, dimethyl, butyl especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., phenoxy or phenoxy substituted with for example methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl, e.g. benzoyl; $C_4$ to $C_8$ cycloalkenyl, e.g., cyclohexenyl; trifluoromethyl; halo, e.g., fluoro or chloro; $C_4$ to $C_5$ heteroaryl, e.g., furyl, pyrrolyl, thienyl; or $C_{10}$ to $C_{14}$ aryl, e.g., naphthyl or naphthyl substituted with $C_1$ to $C_4$ alkyl, e.g., methyl; $C_1$ to $C_4$ alkoxy, e.g., ethoxy, halo; or biphenyl unsubstituted or substituted with methyl or halo, especially fluoro, e.g. 2-(2-fluoro-4-biphenyl). Preferred compounds of formula I are those of the formula:

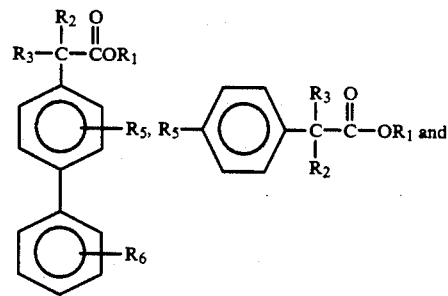

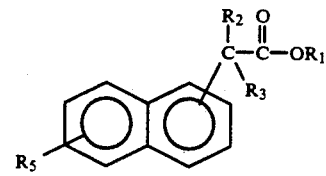

$R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The process of the present invention is particularly applicable to 2-(4-isobutylphenyl)propionic acid and especially in obtaining a preponderance of the S(+) isomer.

The invention is carried out by using a racemic mixture a mixture of both the (+) and (−) or dextro and levo rotatory forms] or a mixture containing a preponderance of one of the enantiomers of these carboxylic acids. (The term "racemic mixture" as used herein is intended to include a range of mixtures of diastereomers from 1:1 through 9.9:1.) The use of racemic mixtures is preferred. However, it should be understood that in this step the process itself does not convert one form of the stereoisomers to the other form but only separates such forms. Further, because the separation of isomers gives rise to a precipitated product largely containing one enantiomer and a liquid phase largely containing the other enantiomer, a high purity salt is obtained that requires a minimum number of recrystallizations (usually not more than two) to yield a product with exceptional high optical purity.

The purified salt obtained from the process of the present invention may be further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even a greater extent.

The first step in the reaction sequence of the present invention is to heat the solid racemic mixture of the aliphatic carboxylic acid (or ester thereof) in order to substantially completely melt it. The temperature of such melt (the first homogeneous melt) will vary depending on the identity of aliphatic carboxylic acid. Typically such first homogenous melt is from about 25° to about 175° C., preferably about 50° to about 100° C.

The first homogeneous melt has added to it an organic or inorganic base, typically, but not necessarily, in an equimolar amount based on the carboxylic acid or esters. When such base is an inorganic one, it is preferred that it is a metallic or ammonium hydroxide, carbonate or bicarbonate, the metal being from Group IA or IIA of the Periodic Table of Elements. Most preferably, the inorganic base is potassium hydroxide.

When the base used in the first step of the separation process is an organic base then it is preferably an aliphatic, aromatic or mixed aliphatic and aromatic amine. The only criteria for such organic base is that it take part in no other reaction with the aliphatic carboxylic acid except salt formation, that it and the salt formed in the reaction with the carboxylic acid be soluble in the melt used in the first step of the present invention. Preferred organic bases are the tri-substituted $C_1$ to $C_6$ linear or branched alkyl amines and the tri-substituted mixed $C_1$ to $C_6$ linear or branched alkyl or $C_6$ to $C_{10}$ arylamines such as triethylamine, phenyl diethylamine and the like.

The addition of such base to the first homogeneous melt produces a second homogeneous melt that is essentially a racemic mixture melt of the salt of the carboxylic acid. At this point in the reaction sequence, i.e., after addition of the organic or inorganic base, the second homogeneous melt may be heated, e.g., to a temperature of about 25° C. to about 100° C., preferably about 50° C. to 75° C. Heating to such temperatures can also be carried out after the chiral organic nitrogenous base is added. Heating is typically carried out, but not limited to, from about 1 to about 16 hours. Preferably from about 2 to about 8 hours. The chiral organic nitrogenous base is added in about a half molar equivalent based on the amount of carboxylic acid salt present in the second homogeneous salt.

The chiral organic nitrogenous base forms a more stable salt with the isomer of the aliphatic carboxylic acid displacing the inorganic or organic base. Additionally, because of the presence of the inorganic or organic base, one of the diastereomeric salts formed from the subsequent displacement of the inorganic or organic base by the chiral organic nitrogenous base is more soluble in the reaction melt mixture (the mixture formed when the chiral base is added to the second homogeneous melt), the other of course precipitates. The solid precipitated is readily separated from the reaction melt mixture by conventional techniques, i.e., centrifugation, filtration and the like.

Generally, the chiral organic nitrogenous base is a $C_1$ to $C_6$ linear or branched aliphatic amine unsubstituted or substituted with $C_6$ to $C_{10}$ aryl group that is unsubstituted or substituted with $C_1$ to $C_6$ alkyl, $C_1$ to $C_6$ alkoxy, $C_1$ to $C_6$ alkoxy or halo. Preferably such chiral organic nitrogenous base is an α-monosubstituted alkylamine, and preferably an α-monosubstituted ethylamine, especially an α-phenylethylamine in which the phenyl ring may be substituted by one or more groups such as alkyl, e.g., $C_{1-4}$ alkyl, especially isopropyl, halogen, e.g., chlorine or fluorine, alkoxy, e.g., $C_{1-4}$, especially methoxy. Particularly preferred bases are (−)-α-methylbenzylamine and (−)-α-(2-methoxyphenyl)ethylamine. Other suitable bases include (−)-α-(4-fluorophenyl)ethylamine, (−)-α-(2-fluorophenyl)ethylamine, (−)-α-(2-fluorophenyl)ethylamine, (−)-α-(2-chlorophenyl)ethyl-amine, (+)-α-(2-methoxyphenyl)ethylamine, (−)-α-(2,6-dimethoxyphenyl)ethylamine and also (+)-α-cyclohexylethylamine.

It should be noted that the process of the present invention is particularly adapted to the economical conversion of racemic mixtures to the diastereomeric S- or (+)- component. (Of course, the R-component may be the least soluble one, in which case the following discussion should be applied in reverse.) The method of the present invention essentially provides a solid precipitate enriched in the S-enantiomer and a liquid phase enriched in the R- or (−)-enantiomer. Liberation of the desired S-enantiomer form the precipitated salt is readily accomplished by acidification of the salt with, for example, dilute mineral acid or any other inorganic or organic acid conventionally known to hydrolyze salts of this nature. While this procedure leaves the liquid phase as a by-product, it can be further treated with acid or base to convert the R-enriched filtrate to the racemic mixture or recover the R-enriched by-product. This mixture can then be reused in the process of the present invention, using the chiral organic base recovered from the above conversion step. Thus, the process of the present invention lends itself readily to a recycling-type of procedure.

It should be noted that the process of the present invention is particularly adapted to the economical conversion of racemic mixtures to the diastereomeric components in the absence of any solvents. The elimination of the solvents eliminates the need for expensive, cumbersome recovery and recycling procedures. It should also be noted that the elimination of solvents or like inert liquids maximizes the through-put or the production of the reactor, i.e., the amount of product made per given volume of the reactor is maximized.

EXAMPLES

The invention is illustrated by the following Examples.

EXAMPLE 1

A flask was charged with ibuprofen (206 grams; 1 mole) and triethylamine (101 grams) and heated to 95° C. under agitation. To the hot solution (S)-methylbenzyl amine (60.5 grams; 0.5 mole) was added over two hours. The reaction mixture was further agitated for two hours and filtered hot. The solids were sucked dry at the buchner and care was taken to maintain the solids at 90°–95° C. The dry solids (140 grams; 85.6% yield on methylbenzyl amine) were acidified and ibuprofen liberated contained 74% S-enantiomer.

EXAMPLE 2

Using the procedure of Example 1, but reducing the (S)-methylbenzyl amine charge to 40 grams (0.33 mole), the precipitated solids (93 grams; 86.0% yield) were acidified and the ibuprofen liberated contained 82% S-enantiomer.

We claim:

1. A process for separating a racemic mixture of an aliphatic carboxylic acid or ester thereof having the formula:

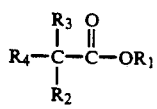

where $R_1$ is hydrogen or $C_1$ to $C_6$ linear or branched alkyl; $R_2$, $R_3$ and $R_4$ are different and are hydrogen or $C_1$ to $C_6$ linear or branched alkyl; cycloalkyl; alkyl-substituted cycloalkyl; $C_6$ to $C_{14}$ aryl; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; or $C_4$ to $C_5$ heteroaryl; which comprises:
  i) heating a solid, racemic mixture of said aliphatic carboxylic acid or ester thereof to a temperature sufficient to produce a first homogeneous melt;
  ii) adding an inorganic or organic base to said first homogeneous melt thereby producing a second homogeneous melt;
  iii) treating said second homogeneous melt with a chiral organic nitrogenous base;
  iv) precipitating from the reaction melt mixture formed in step iii) a solid salt that is the reaction product of the chiral organic nitrogenous base and one of the diastereomers in said racemic mixture of the aliphatic carboxylic acid or ester thereof; and
  v) separating the precipitated salt.

2. The process according to claim 1 wherein said aliphatic carboxylic acid thereof is a 2-arylpropionic acid derivative thereof.

3. The process according to claim 2 wherein said ester is a $C_1$ to $C_6$ linear or branched ester.

4. The process of claim 1 wherein said base is an inorganic base.

5. The process according to claim 4 wherein said inorganic base is a metallic hydroxide, carbonate or bicarbonate, said metal being from Group IA or IIA of the Periodic Table of Elements.

6. The process according to claim 5 wherein said inorganic base is potassium hydroxide.

7. The process of claim 1 wherein said chiral organic nitrogenous base is a $C_1$ to $C_6$ linear or branched aliphatic amine or a $C_1$ to $C_6$ linear or branched aliphatic amine further substituted with a $C_6$ to $C_{10}$ aryl group that is unsubstituted or substituted with $C_1$ to $C_6$ alkyl, $C_1$ to $C_6$ alkoxy or halo, or $C_1$ to $C_6$ linear or branched alkoxy.

8. The process according to claim 5 wherein said chiral organic nitrogenous base is an α-monosubstituted alkylamine.

9. The process according to claim 6 wherein said chiral organic nitrogenous base is (−)alpha-methylbenzylamine.

10. The process of claim 7 wherein the temperature sufficient to produce said first homogeneous melt is from about 25° to about 175° C.

11. The process of claim 10 wherein said temperature is from about 50° to about 100° C.

12. The process of claim 11 wherein said second homogeneous melt is treated with the chiral organic nitrogenous base at a temperature of from about 25° to about 100° C.

13. The process according to claim 12 wherein said treatment is carried out over a period of from about 1 hour to about 16 hours.

14. A process for separating a racemic mixture of an aliphatic carboxylic acid or ester thereof having the formula:

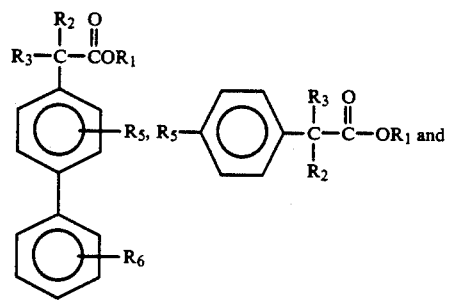

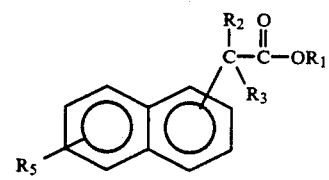

where $R_1$ is hydrogen or $C_1$ to $C_6$ linear or branched alkyl; $R_2$, $R_3$ and $R_4$ are different and are hydrogen or $C_1$ to $C_6$ linear or branched alkyl; cycloalkyl; alkyl-substituted cycloalkyl; $C_6$ to $C_{14}$ aryl; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; or $C_4$ to $C_5$ heteroaryl; and $R_5$ and $R_6$ are $C_1$ to $C_4$ linear or branched alkyl, $C_1$ to $C_4$ linear or branched alkoxy or halo which comprises:
  i) heating a solid, racemic mixture of said aliphatic carboxylic acid or ester thereof to a temperature sufficient to produce a first homogeneous melt;
  ii) adding an inorganic or organic base to said first homogeneous melt thereby producing a second homogenous melt;
  iii) treating said second homogenous melt with a chiral organic nitrogenous base;
  iv) precipitating from the reaction melt mixture formed in step iii) a solid salt that is the reaction product of the chiral organic nitrogenous base and one of the diastereomers in said racemic mixture of the aliphatic carboxylic acid or ester thereof; and
  v) separating the precipitated salt.

15. The process of claim 14 wherein said aliphatic carboxylic acid is 2-(4-isobutylphenyl)propionic acid.

16. The process of claim 14 wherein the mole ratios of the aliphatic carboxylic acid to the chiral organic nitrogenous base is from about 1 to 0.1 to about 0.1 to 1.

17. The process of claim 15 wherein the reaction mixture has a liquid phase comprising from about 50% to about 100% of the other diastereomeric salt.

18. The process of claim 16 wherein the mole ratios of the aliphatic carboxylic acid to the chiral organic nitrogenous base is from about 1 to 0.5 to about 1 to 1.

19. A process for separating a racemic mixture of an aliphatic carboxylic acid or ester thereof having the formula:

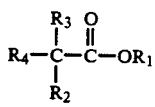

wherein $R_1$ is hydrogen or $C_1$ to $C_6$ linear or branched alkyl; $R_2$, $R_3$ and $R_4$ are methyl or ethyl; benzyl; cyclopropyl; cyclobutyl; cyclopentyl; cyclohexyl; methylcyclohexyl; phenyl unsubstituted or substituted with methyl, dimethyl, butyl, isobutyl $C_1$ to $C_4$ alkylthio, $C_1$ to $C_4$ alkoxy, cyano, fluoro or chloro; phenoxy or phenoxy substituted with methyl, dimethyl, butyl or isobutyl, $C_1$ to $C_4$ alkylthio, $C_1$ to $C_4$ alkoxy, cyano or halo; methylthio, benzoyl; cyclohexenyl; trifluoromethyl; fluoro; chloro; furyl; pyrrolyl; thienyl; naphthyl or naphthyl substituted with methyl, ethoxy or halo; or biphenyl unsubstituted or substituted with methyl or fluoro which comprises:

i) heating a solid, racemic mixture of said aliphatic carboxylic acid or ester thereof to a temperature sufficient to produce a first homogeneous melt;

ii) adding an inorganic or organic base to said first homogeneous melt thereby producing a second homogeneous melt;

iii) treating said second homogeneous melt with a chiral organic nitrogenous base;

iv) precipitating from the reaction melt mixture formed in step iii) a solid salt that is the reaction product of the chiral organic nitrogenous base and one of the diastereomers in said racemic mixture of the aliphatic carboxylic acid or ester thereof; and v) separating the precipitated salt.

20. A method for separating the diastereomers in a racemic mixture of 2-(4-isobutylphenyl)propionic acid comprising:

i) heating solid, racemic 2-(4-isobutylphenyl)propionic acid to a temperature sufficient to produce a first homogeneous melt;

ii) adding to said first homogeneous melt an organic or inorganic base thereby producing a second homogeneous melt;

iii) treating sad second homogeneous melt with a chiral organic nitrogenous base;

iv) precipitating from the reaction melt solution formed in step iii) a solid salt that is reaction product of the chiral organic nitrogenous base and one of the diastereomers of 2-(4-isobutylphenyl)propionic acid; and v) separating the precipitated solid salt.

21. The process of claim 20 wherein said separated salt is hydrolyzed and the free optically active 2-(4-isobutylphenyl)propionic acid and the chiral amine are recovered.

22. The process of claim 21 wherein said optically active 2-(4-isobutylphenyl)propionic acid has S(+) configuration.

23. The process of claim 20 wherein a liquid phase is obtained after separation of the precipitated salt containing the R-enantiomer and said liquid phase is treated to racemize said salt of R-enantiomer into the salt of racemic (R,S) mixture for recycling.

* * * * *